(12) United States Patent
Ini et al.

(10) Patent No.: US 7,915,412 B2
(45) Date of Patent: Mar. 29, 2011

(54) PROCESS FOR THE SYNTHESIS OF 9-HYDROXY RISPERIDONE (PALIPERIDONE)

(75) Inventors: Santiago Ini, Haifa (IL); Naama Chasid, Petach Tikva (IL); Yaron Shmuely, Hedera (IL); Kobi Chen, Kfar-Saba (IL)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 0 days.

(21) Appl. No.: 11/889,557

(22) Filed: Aug. 14, 2007

(65) Prior Publication Data

US 2008/0171875 A1    Jul. 17, 2008

Related U.S. Application Data

(60) Provisional application No. 60/963,019, filed on Aug. 1, 2007, provisional application No. 60/935,093, filed on Jul. 26, 2007, provisional application No. 60/928,745, filed on May 10, 2007, provisional application No. 60/839,428, filed on Aug. 23, 2006, provisional application No. 60/837,804, filed on Aug. 14, 2006.

(51) Int. Cl.
C07D 239/70 (2006.01)

(52) U.S. Cl. ...................................................... 544/282
(58) Field of Classification Search ................... 544/282
See application file for complete search history.

(56) References Cited

U.S. PATENT DOCUMENTS

| 4,804,663 | A | 2/1989 | Kennis et al. |
| 5,158,952 | A | 10/1992 | Janssen et al. |
| 5,688,799 | A | 11/1997 | Vandenberk et al. |
| 2006/0004199 | A1 | 1/2006 | Reddy et al. |

FOREIGN PATENT DOCUMENTS

| WO | WO 01/85731 | 11/2001 |
| WO | WO 02/12200 | 2/2002 |
| WO | WO 2005/030772 | 4/2005 |
| WO | WO 2007/093870 | 8/2007 |

OTHER PUBLICATIONS

Third Party Observations received for European Application 07811310.7, dated Oct. 31, 2008.
International Search Report of PCT International Application No. PCT/US2007/017955, dated May 8, 2008.

*Primary Examiner* — James O Wilson
*Assistant Examiner* — Cecilia M Jaisle
(74) *Attorney, Agent, or Firm* — Kenyon & Kenyon LLP

(57) ABSTRACT

The present invention relates to a process for preparing paliperidone from its intermediate 3-(2-chloroethyl)-6,7,8,9-tetrahydro-9-hydroxy-2-methyl-4H-pyrrido[1,2-a]-pyrimidin-4-one.

20 Claims, No Drawings

PROCESS FOR THE SYNTHESIS OF 9-HYDROXY RISPERIDONE (PALIPERIDONE)

CROSS REFERENCE TO RELATED APPLICATIONS

This patent application claims the benefits of U.S. Provisional Application No. 60/837,804 filed Aug. 14, 2006, No. 60/928,745 filed May 10, 2007, No. 60/935,093 filed Jul. 26, 2007, No. 60/839,428 filed Aug. 23, 2006 and No. 60/963,019 filed on Aug. 1, 2007, the disclosures of which are hereby incorporated by reference.

FIELD OF THE INVENTION

The invention concerns a process for the synthesis of 9-hydroxy risperidone (Paliperidone).

BACKGROUND OF THE INVENTION

Paliperidone, 3-[2-[4-(6-fluorobenzo[d]isoxazol-3-yl)-1-piperidyl]ethyl]-7-hydroxy-4-methyl-1,5-diazabicyclo[4.4.0]deca-3,5-dien-2-one, is a 5-HT antagonist belonging to the chemical class of benzisoxazole derivatives and a racemic mixture having the following structural formula:

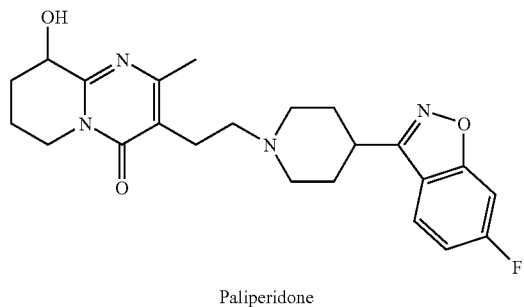

Paliperidone

Paliperidone is a metabolite of Risperidone. Marketed under the name, Invega®, Paliperidone is a psychotropic agent approved in the United States for the treatment of schizophrenia.

A process for the synthesis of Paliperidone, is described in U.S. Pat. No. 5,158,952 according to the following scheme.

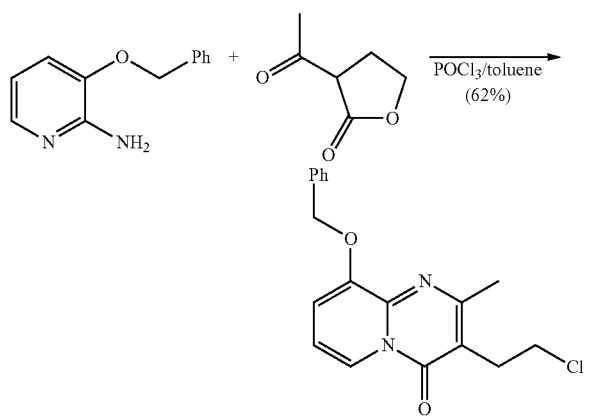

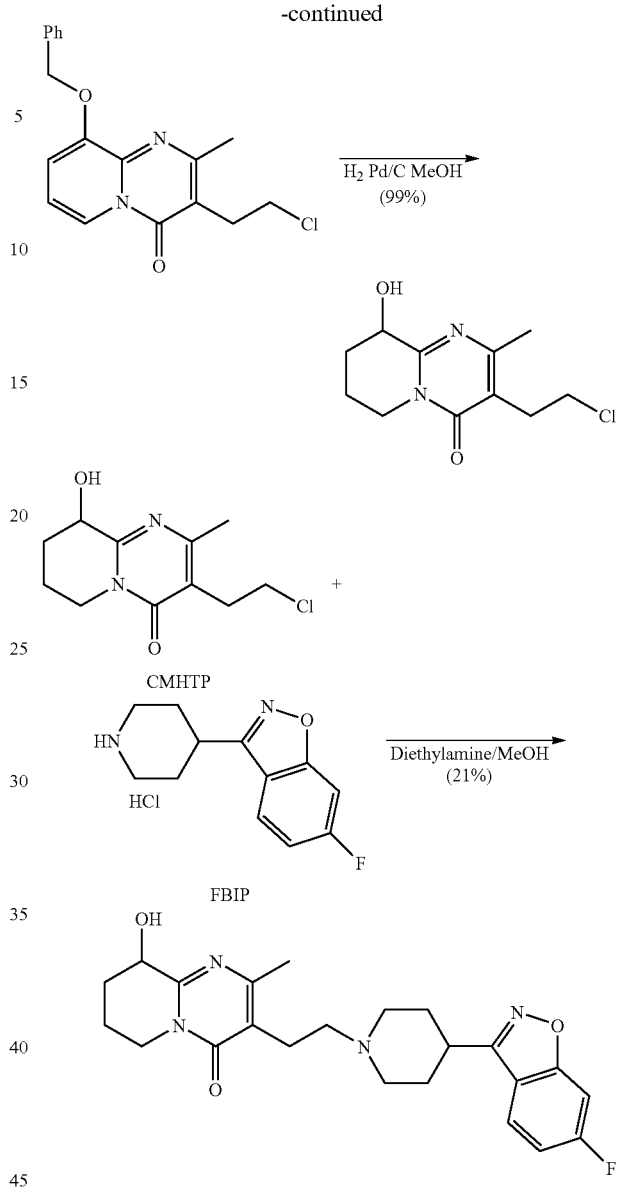

The preparation of paliperidone via the intermediate 3-(2-chloroethyl)-6,7,8,9-tetrahydro-9-hydroxy-2-methyl-4H-pyrido[1,2-a]-pyrimidin-4-one (CMHTP) is depicted in the last step of the above scheme. This process is performed in the presence of an organic base.

A process for the synthesis of CMHTP is described also in U.S. Pat. No. 5,688,799.

The processes described in the above publications are long, and result in low chemical yields, making their application in the industry very hard. There is a need in the art for a new process for preparing Paliperidone and its intermediates.

SUMMARY OF THE INVENTION

In one embodiment, the present invention provides a process for preparing paliperidone by combining 3-(2-chloroethyl)-6,7,8,9-tetrahydro-9-hydroxy-2-methyl-4H-pyrido[1,2-a]-pyrimidin-4-one (CMHTP) or a salt thereof and 6-fluoro-3-(4-piperidinyl)-1,2-benisoxazole (FBIP) or a salt thereof in the presence of an inorganic base.

In a preferred embodiment, the process is performed in the presence of a solvent. In another preferred embodiment, the process is performed under nitrogen.

DETAILED DESCRIPTION OF THE INVENTION

As used herein, Paliperidone is equivalent to 9-hydroxy risperidone.

As used herein, "room temperature" relates to a temperature of about 20° to about 25° C.

The present invention provides a process for preparing paliperidone by reacting 3-(2-chloroethyl)-6,7,8,9-tetrahydro-9-hydroxy-2-methyl-4H-pyrido[1,2-a]-pyrimidin-4-one (CMHTP) or a salt thereof with 6-fluoro-3-(4-piperidinyl)-1,2-benisoxazole (FBIP) or a salt thereof, in the presence of an inorganic base. For instance, the process for preparing paliperidone can be conducted as described in the following scheme:

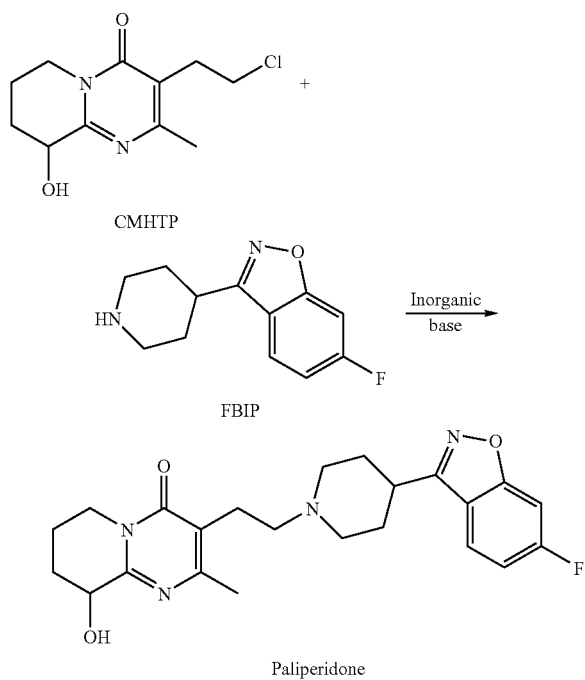

In one embodiment, a mixture of CMHTP, FBIP and an inorganic base are reacted. Preferably, the reaction occurs in the presence of a solvent. The solvent is preferably selected from the list consisting of: water, $C_{1-8}$ alkyl alcohols, acetonitrile, $C_{3-6}$ amides, $C_{3-6}$ ketones, $C_{5-12}$ aromatic hydrocarbons, $C_{2-6}$ alkyl acetates and $C_{2-8}$ ethers. Preferred $C_{1-4}$ alkyl alcohols are methanol, ethanol, n-propanol, isopropanol (IPA), n-butanol, isobutanol and 2-butanol. Preferred $C_{3-6}$ amides are dimethylacetamide and dimethylformamide (DMF). Preferred $C_{3-6}$ ketones are acetone, methyl ethyl ketone (MEK) and methyl iso-butyl ketone (MIBK). Preferred $C_{6-12}$ aromatic hydrocarbons are benzene, toluene and xylene. Preferred $C_{2-6}$ alkyl acetates are ethyl acetate and isobutyl acetate. Preferred $C_{2-8}$ ethers are tetrahydrofurane (THF), diethoxymethane (DEM), isobutyl methyl ether, dibutyl ether and polyethylene glycol (PGME). More preferably, the solvent is water, acetonitrile, IPA or DMF. Even more preferably, the solvent is selected from IPA and acetonitrile, and most preferably, the solvent is acetonitrile.

In the process of the present invention for preparing paliperidone, the inorganic base used can be in a ratio of about 1 to about 3 moles of the inorganic base per mole of CMHTP such as about 2.5 moles of the inorganic base per mole of CMHTP. The amount of the inorganic base used, preferably, is in a molar ratio of about 2, i.e., about 2 moles of the inorganic base per mole of CMHTP, such as about 1.8 moles of the inorganic base per mole of CMHTP.

Examples of the inorganic base that can be used in the process for preparing paliperidone of the invention can include sodium carbonate, potassium carbonate, sodium bicarbonate and potassium bicarbonate.

The advantages of working in the presence of an inorganic base are that there is no need to dispose of the organic waste that is formed during this process. This advantage is especially relevant to industrial applicability.

Preferably, the reaction occurs under nitrogen, in order to avoid the color formation, attributed to impurities. This results in a final paliperidone that has higher purity.

The reaction may be performed in the presence of a salt such as potassium iodide, potassium bromide, sodium iodide and sodium bromide in order to accelerate the reaction, and also increase yield.

Also, a phase transfer catalyst (PTC) may be present as well, in order to facilitate the reaction, which is performed in a two-phase system. Typically, the phase transfer catalyst is selected from the group consisting of tetraalkylammonium halides, tetraarylammonium halides, and tetra(alkyl)(aryl) ammonium halides, wherein the alkyl and aryl are the same or different. Preferably the alkyl is $C_{1-6}$ alkyl. Preferably, the aryl is $C_{6-10}$ aryl. Preferably, the halide is chloride, bromide or iodide. The phase transfer catalyst is preferably selected from the group consisting of tetrabutylammonium bromide or tetrabutylammonium iodide.

Typically, the obtained reaction mixture is heated, preferably to a temperature of about 60° C. to about reflux, most preferably to a temperature of about 65° C. The heated mixture is preferably maintained for at least about 8 hours, for the reaction to take place. Preferably, the reaction mixture is maintained for at least about 24 hours, and most preferably, for at least about 40 hours.

Subsequently, the reaction mixture is cooled. Preferably the cooling is gradual, to about room temperature, and then to a temperature of below 0° C., preferably to a temperature of about −10° C. The cooling to the preferred temperature of −10° C. may be done either relatively quickly, e.g. over about 30 minutes, or alternatively, over a longer period of time, such as about 6 hours, especially for large quantities for industrial scale.

After the cooling step, solid paliperidone is formed, which is then recovered by methods known in the art. Preferably, the obtained paliperidone is first washed with an organic solvent, which is the organic solvent used in the reaction, such as acetonitrile, acetone, dichloromethane or IPA, followed by drying. Preferably, the drying is performed at about 60° C. for about 1 hour.

Both CMHTP and FBIP starting materials can be in the form of a base or acid salts. Most preferred salt is a hydrochloride salt. CMHTP may be obtained by any method known in the art, such as the ones described in U.S. Pat. No. 5,158,952. The FBIP starting material is commercially available.

The crude paliperidone may be purified, for example, by recrystallization such as recrystallization from acetonitrile. The obtained crystalline form is preferably paliperidone Form I, characterized by powder X-ray diffraction (PXRD) pattern having peaks at about: 10.1, 12.4, 14.3, 17.0 and 17.2±0.2 degrees two theta, wherein the PXRD pattern may have further peaks at about 12.9, 18.9, 21.9, 24.8 and 26.2±0.2 degrees two-theta.

Having described the invention with reference to certain preferred embodiments, other embodiments will become apparent to one skilled in the art from consideration of the specification. The invention is further defined by reference to the following examples describing in detail the synthesis of 9-hydroxy risperidone. It will be apparent to those skilled in the art that many modifications, both to materials and methods, may be practiced without departing from the scope of the invention.

EXAMPLES

Example 1

A mixture of CMHTP (4.393 g, 0.0168 mol), FBIP (4.695 g, 0.0203 mol), sodium carbonate (4.968 g, 0.0422 mol) and potassium iodide (0.288 g, 0.0017 mol) in DMF (50 ml) was heated for 8 h at 85° C. The mixture was poured into water (500 ml) and extracted with DCM (4×100 ml). The extracts were combined, washed with water (4×100 ml), dried with anhydrous magnesium sulfate, filtered and evaporated under reduced pressure to afford the crude title product. Crystallization from acetonitrile (100 ml) afforded 4.63 g of the title product, in a purity of >90%. Yield 58%.

Example 2

A 100 ml flask equipped with a mechanical stirrer, a reflux condenser was charged under nitrogen with CMHTP (2 g), FBIP (1.92 g), sodium carbonate (1.6 g), potassium iodide (0.03 g) and isopropyl alcohol (20 ml). The suspension was heated to 65° C. and stirred for 24 hours to obtain yellowish slurry. The reaction mixture was cooled to −10° C. in 2 hours, then filtered under reduced pressure and rinsed with 3 portions of isopropyl alcohol (10 ml each). The resulting solid was slurried 3 times with water (3×20 ml) and 3 times with acetone (3×10 ml), filtered and dried at room temperature for 1 hour and at 60° C. under reduced pressure for 1 hour to obtain Paliperidone (1.84 g, 57.7%).

Example 3

A 100 ml flask equipped with a mechanical stirrer, a reflux condenser was charged under nitrogen with CMHTP (5 g), FBIP (4.8 g), Sodium carbonate (4.0 g) and iso-Propyl alcohol (50 ml). The suspension was heated to 65° C. and stirred for 30 hours to obtain yellowish slurry. The reaction mixture was cooled to room temperature and was left over night while stirring, then cooled to −10° C. in 30 minutes, filtered under reduced pressure, rinsed 3 times with iso-Propyl alcohol (10 ml each) and dried in oven at 60° C. under reduced pressure for 1 hour to give Paliperidone.

Example 4

A 100 ml flask equipped with a mechanical stirrer, a reflux condenser was charged under nitrogen with CMHTP (5 g), FBIP (4.8 g), Sodium carbonate (4.0 g), Tetrabutylammonium bromide (0.6 g) and iso-Propyl alcohol (50 ml). The suspension was heated to 65° C. and stirred for 24 hours to obtain yellowish slurry. The reaction mixture was cooled to room temperature and was stirred for 3 hours, then cooled to (−10° C.) in 30 minutes, filtered under reduced pressure, rinsed 3 times with iso-Propyl alcohol (10 ml each) and dried in oven at 60° C. under reduced pressure for 1 hour to give Paliperidone.

Example 5

A 100 ml flask equipped with a mechanical stirrer, a reflux condenser was charged under nitrogen with CMHTP (5 g), FBIP (4.8 g), Sodium carbonate (4.0 g), Tetrabutylammonium bromide (0.6 g) and n-Butyl alcohol (30 ml). The suspension was heated to reflux temperature and stirred for 24 hours to obtain a dark purple suspension. The presence of Paliperidone was observed by HPLC.

Example 6

A 100 ml flask equipped with a mechanical stirrer, a reflux condenser was charged under nitrogen with CMHTP (5 g), FBIP (4.8 g), Sodium carbonate (4.0 g), Tetrabutylammonium iodide (0.7 g) and iso-Propyl alcohol (50 ml). The suspension was heated to 65° C. and stirred for 26 hours to obtain an orange slurry. The reaction mixture was cooled to room temperature and was stirred for 2 hours, then cooled to (−10° C.) in 30 minutes, filtered under reduced pressure, rinsed 3 times with iso-Propyl alcohol (10 ml each) and dried in oven at 60° C. under reduced pressure for 1 hour to give Paliperidone.

Example 7

A 100 ml flask equipped with a mechanical stirrer, a reflux condenser was charged under nitrogen with CMHTP (5 g), FBIP (5.8 g), Sodium carbonate (4.8 g) and iso-Propyl alcohol (50 ml). The suspension was heated to 65° C. and stirred for 26 hours to obtain yellow slurry. The reaction mixture was cooled to room temperature and was stirred for 2 hours, then cooled to (−10° C.) in 30 minutes, filtered under reduced pressure, rinsed 3 times with iso-Propyl alcohol (10 ml each) and dried in oven at 60° C. under reduced pressure for 1 hour to give Paliperidone.

Example 8

A 250 ml reactor equipped with a mechanical stirrer, a reflux condenser was charged under nitrogen with CMHTP (10 g), FBIP (9.6 g), Potassium carbonate (10.4 g) and iso-Propyl alcohol (100 ml). The suspension was heated to 65° C. and stirred for 28 hours to obtain dark yellow slurry. The reaction mixture was cooled to room temperature and was stirred for 2 hours, then cooled to (−10° C.) in 30 minutes, filtered under reduced pressure, rinsed 3 times with iso-Propyl alcohol (10 ml each) and dried in oven at 60° C. under reduced pressure for 1 hour to give Paliperidone.

Example 9

A 250 ml 3-necked flask equipped with a mechanical stirrer and a reflux condenser was charged under nitrogen with CMHTP (10 g), FBIP (9.6 g), Sodium carbonate (7.96 g) and water (100 ml). The suspension was heated to 65° C. and stirred for 5 hours to obtain light brown slurry. The reaction mixture was cooled to room temperature and was stirred for 1 hour, filtered under reduced pressure, rinsed 3 times with water (20 ml each) and dried in oven at 50° C. under reduced pressure overnight, resulting in 11.31 g of Paliperidone.

Example 10

A 250 ml reactor equipped with a mechanical stirrer, a reflux condenser was charged under nitrogen with CMHTP (20 gr), FBIP (19.2 gr), Sodium carbonate (16 gr) and acetonitrile (200 ml). The suspension was heated to 65° C. and stirred for 26.5 hours. The reaction mixture was cooled to −10° C., filtered under reduced pressure, and washed 3 times with acetonitrile (3×40 ml each). The resulting solid was slurried in 200 ml water at room temperature, filtered under reduced pressure, washed 3 times with water (3×80 ml each), and with 40 ml acetone. The crude was dried in a vacuum oven at 50° C. under reduced pressure for overnight to give 29 gr of Paliperidone.

Example 11

A 100 ml flask equipped with a mechanical stirrer, a reflux condenser was charged under nitrogen with CMHTP (5 g), FBIP (4.8 g), Sodium carbonate (4.0 g), potassium bromide (0.22 g) and acetonitrile (50 ml). The suspension was heated to 65° C. and stirred for about 26 hours. The reaction mixture was cooled to room temperature, vacuums filtrated, rinsed with water (3 times) and acetone and dried in oven at 55° C. under reduced pressure for overnight to give Paliperidone.

Example 12

A 250 ml reactor equipped with a mechanical stirrer, a reflux condenser was charged under nitrogen with 80 ml. acetonitrile (the solvent was degassed passing through nitrogen for five minutes), CMHTP (7.5 gr), FBIP (8 gr), and sodium carbonate (6.6 gr). The suspension was heated to 65° C. and additional heated to 85° C. during 12 hours, and maintained at the same temperature for an additional 12 hours. The reaction mixture was cooled to 0° C., filtered under reduced pressure, and washed 3 times with acetonitrile. The resulting solid was slurried in 56 ml water at room temperature, filtered under reduced pressure, washed 4 times with water, and with 40 ml acetone. The crude was dried in a vacuum oven at 55° C. under reduced pressure for overnight to give Paliperidone.

Example 13

A 100 ml flask equipped with a mechanical stirrer, a reflux condenser was charged under nitrogen with CMHTP (5.0 g), FBIP (4.81 g), sodium carbonate (3.97 g), the indicated salt and acetonitrile (50 ml) and stirred at room temperature for 19 hours. The slurry was heated to 50° C. and stirred at this temperature for 8 hours, and then at room temperature for another 94 hours.

| Experiment | Salt | Weight of salt (g) | % conversion |
| --- | --- | --- | --- |
| 23 | NaI | 0.28 | 17.8 |
| 24 | KI | 0.31 | 33.8 |
| 25 | NaBr | 0.19 | 29.1 |
| 26 | KBr | 0.22 | 38.2 |

Example 14

A 100 ml flask equipped with a mechanical stirrer, a reflux condenser was charged under nitrogen with CMHTP (5 g), FBIP (4.81 g), sodium carbonate (3.97 g), potassium bromide (0.22 g) and acetonitrile (50 ml). The suspension was heated to 65° C. and stirred for 24 hours. The reaction mixture was cooled to 0° C., filtered under reduced pressure and rinsed with acetonitrile. The resulting solid was slurried with water (3×15 ml), washed with water and acetone. The solid was dried in a vacuum oven at 55° C. overnight to give 7.12 g of Paliperidone.

Example 15

A 100 ml flask equipped with a mechanical stirrer, a reflux condenser was charged under nitrogen with CMHTP (5.0 g), FBIP (4.81 g), sodium carbonate (3.97 g), the indicated additive and acetonitrile (50 ml) and stirred at room temperature for 15 hours. The slurry was heated to 50° C. and stirred at this temperature for 9 hours, and then at room temperature for another 43 hours.

| Experiment no. | Additive | Quantity (g) | % conversion |
| --- | --- | --- | --- |
| 28 | Tetramethylammonium iodide (TMAI) | 0.38 | 21.5 |
| 29 | Tetrabutylammonium bromide (TBAB) | 0.60 | 19.2 |
| 30 | Tridodecylmethyl-ammonium iodide (TDMAI) | 1.24 | 18.3 |
| 31 | Tetrabutylammonium iodide (TBAI) | 0.69 | 23.3 |

Example 16

A 100 ml flask equipped with a mechanical stirrer, a reflux condenser was charged under nitrogen with CMHTP (5 g), FBIP (4.81 g), sodium carbonate (3.97 g), TBAI (0.69 g) and acetonitrile (50 ml). The suspension was heated to 65° C. and stirred for 24 hours. The reaction mixture was cooled to 0° C., stirred for 2 hours, filtered under reduced pressure and rinsed with acetonitrile. The resulting solid was slurried with water (3×15 ml), washed with water and acetone. The solid was dried in a vacuum oven at 55° C. overnight to give 6.62 g of Paliperidone.

The invention claimed is:
1. A process for preparing paliperidone comprising
   a) combining 3-(2-chloroethyl)-6,7,8,9-tetrahydro-9-hydroxy-2-methyl-4H-pyrido[1,2-a]-pyrimidin-4-one (CMHTP) or salt thereof, 6-fluoro-3-(4-piperidinyl)-1,2-benisoxazole (FBIP) or salt thereof, an inorganic base, and a first solvent to obtain a suspension;
   b) heating the suspension to obtain a reaction mixture;
   c) cooling the reaction mixture;
   d) filtering the cooled reaction mixture of step c) to obtain a solid;
   e) adding a second solvent to the solid of step d) to obtain a slurry; and
   f) filtering the slurry to obtain paliperidone.
2. The process of claim 1, wherein the inorganic base is sodium carbonate or potassium carbonate.
3. The process of claim 2, wherein the inorganic base is sodium carbonate.
4. The process of claim 1, wherein the first and second solvents are selected from the group consisting of water, $C_{1-4}$ alkyl alcohols, acetonitrile, $C_{3-6}$ amides, $C_{3-6}$ ketones, $C_{6-12}$ aromatic hydrocarbons, $C_{2-6}$ alkyl acetates and $C_{2-8}$ ethers.
5. The process of claim 4, wherein the first and second solvents are selected from the group consisting of water, acetonitrile, methanol, ethanol, n-propanol, isopropanol, n-butanol, isobutanol, 2-butanol, dimethylacetamide, dimethylformamide, acetone, methyl ethyl ketone, methyl iso- butyl ketone, benzene, toluene, xylene, ethyl acetate, isobutyl acetate, tetrahydrofurane, isobutylmethyl ether, dibutyl ether and polyethylene glycol.

6. The process of claim 1, wherein the first solvent is selected from isopropyl alcohol and acetonitrile.

7. The process of claim 6, wherein the first solvent is acetonitrile.

8. The process of claim 1, wherein the second solvent is water.

9. The process of claim 1, wherein step a) is performed under nitrogen.

10. The process of claim 1, wherein step a) further comprises adding a salt together with the CMHTP or salt thereof, FBIP or salt thereof, inorganic base, and first solvent to obtain the suspension, wherein the salt is selected from the group consisting of potassium iodide, potassium bromide, sodium bromide and sodium iodide.

11. The process of claim 1, wherein step a) further comprises adding a phase transfer catalyst together with the CMHTP or salt thereof, FBIP or salt thereof, inorganic base, and first solvent to obtain the suspension, wherein the phase transfer catalyst is selected from the group consisting of tetraalkylammonium halides, tetraarylammonium halides, and tetra(alkyl)(aryl) ammonium halides, wherein the alkyl and aryl groups are the same or different.

12. The process of claim 11, wherein the phase transfer catalyst is selected from the group consisting of tetramethylammonium iodide, tridodecylmethylammonium iodide, tetrabutylammonium bromide and tetrabutylammonium iodide.

13. The process of claim 1, wherein the heating step b) comprises heating to a temperature of about 60° C. to about reflux.

14. The process of claim 13, wherein the heating step b) comprises heating to a temperature of about 65° C.

15. The process of claim 1, wherein the cooling step c) comprises cooling for a period of about 30 minutes to about 6 hours.

16. The process of claim 1, wherein the cooling step c) comprises cooling to about room temperature, and subsequently cooling to a temperature of below 0° C.

17. The process of claim 16, wherein the subsequent cooling is to a temperature of about −10° C.

18. The process of claim 1, wherein the filtering step d) further comprises washing the solid with acetonitrile.

19. The process of claim 1, wherein the filtering step f) further comprises washing with water or an organic solvent or mixture thereof followed by drying.

20. The process of claim 19, wherein the organic solvent is acetone.

* * * * *